United States Patent
Da Frota Carrera

(10) Patent No.: US 7,993,379 B2
(45) Date of Patent: Aug. 9, 2011

(54) BONE FASTENING PLATE

(76) Inventor: Eduardo Da Frota Carrera, São Paulo (BR)

(*) Notice: Subject to any disclaimer, the term of this patent is extended or adjusted under 35 U.S.C. 154(b) by 618 days.

(21) Appl. No.: 11/595,222

(22) Filed: Nov. 10, 2006

(65) Prior Publication Data
US 2008/0114360 A1 May 15, 2008

(51) Int. Cl.
*A61B 17/80* (2006.01)
(52) U.S. Cl. .......... 606/280; 606/282; 606/286
(58) Field of Classification Search .......... 606/70–71, 606/280–299, 902–906
See application file for complete search history.

(56) References Cited

U.S. PATENT DOCUMENTS

| | | | | |
|---|---|---|---|---|
| 2,737,835 A * | 3/1956 | Herz | ............................. | 606/101 |
| 4,800,874 A * | 1/1989 | David et al. | ................... | 606/286 |
| 4,966,599 A * | 10/1990 | Pollock | ......................... | 606/915 |
| 5,113,685 A * | 5/1992 | Asher et al. | ...................... | 72/458 |
| 6,183,475 B1 * | 2/2001 | Lester et al. | .................. | 606/281 |
| 6,221,075 B1 * | 4/2001 | Tormala et al. | ................. | 606/77 |
| 6,364,881 B1 * | 4/2002 | Apgar et al. | .................. | 606/284 |
| 7,537,604 B2 * | 5/2009 | Huebner | ........................ | 606/281 |
| 2005/0010226 A1 * | 1/2005 | Grady et al. | .................... | 606/69 |
| 2005/0143736 A1 * | 6/2005 | da Frota Carrera | ............ | 606/60 |
| 2005/0171544 A1 * | 8/2005 | Falkner | .......................... | 606/69 |
| 2006/0089648 A1 * | 4/2006 | Masini | ............................ | 606/69 |
| 2007/0173835 A1 * | 7/2007 | Medoff | ........................... | 606/62 |

* cited by examiner

*Primary Examiner* — Thomas C. Barrett
*Assistant Examiner* — Andrew Yang
(74) *Attorney, Agent, or Firm* — Volpe and Koenig, P.C.

(57) ABSTRACT

The present invention refers to a fastening plate to be used in bones, more specifically, to a plate whose shape and arrangement of screws promote the fastening and keeping of fractured bones or bones that have undergone osteotomy in adequate position, angle and inclination.

5 Claims, 3 Drawing Sheets

BONE FASTENING PLATE

FIELD OF THE INVENTION

The present invention is related to a bone fixing plate, more specifically, a plate that, besides fastening, corrects and supports the fractured bone fragments in the position pre-established by the blade angle of the plate.

SUMMARY

The main objective of this invention is to fasten fractured bones or bones that have undergone osteotomy (i.e., bones that are sawed in order to be relocated to correct any pre-existing deformity).

The objective of the current treatment of fractures is, among other things, to fasten and stabilize displaced bone fragments in their correct (or anatomic) position. The purpose, therefore, is to find a device that promotes the best possible fastening and stabilization of the fractured fragments. Although the plates currently used for the treatment of fractures promote good fastening and stabilization, they may fail because of the improper positioning of the fractured fragments, depending on the kind of fracture.

The innovation shown herein refers to a type of shape of angled plate-blades with holes throughout their length, which allow the stabilization and fastening of fractured bone fragments. The plate shape in one of its ends consists of angles that provide a different aspect from other existing plates for the treatment of fractures. In addition, there may be three special holes, one in each plate segment that may be linked to each other through a screw in order to fasten one or more fractured bone fragments. Besides this central hole at the end of the plate blade, there may be other holes, as many as required, to fasten the fractured bone fragments or bones that have undergone osteotomy.

The plate is introduced and fastened to the human bone, between the fractured fragments, to promote the correction of these fragments and their maintenance in a desired position.

The present invention is comprised of an angled metal plate-blade, or biocompatible material (with varied angles for each type of fracture—initially blades with angles of about 60° in the first curvature in relation to the longest blade, and another more distal angle in relation to the longest blade, of about 45° in relation to the longest blade) to fasten bone segments. The material is S-shaped at the end where the plate is subject to bending.

The invention can be considered as having an upper portion that corresponds to the end where the curvatures are, and a lower and longer portion where there is no bending of the material. The upper portion (of the plate curvatures) is considered and referred to as "blade" and the lower portion (longer and straight) is considered and referred to as "plate".

The blade has two curvatures so that the angle formed between the blade more distant from the plate and the plate is of about 45°. The blade may have a hole or side expansions for the insertion of screws. The blade is used to support and fasten the fractured bone fragments and may remain inside the bone tissue after the correction of the fragments.

The plate that corresponds to the longest straight segment, which has no curves, has two or more holes, through which screws are passed to fix it to the bone.

BRIEF DESCRIPTION OF THE FIGURES

The present invention will be better understood with the figures, attached hereto, shown here merely as an example, and not as a limitation, where.

DETAILED DESCRIPTION OF THE PREFERRED EMBODIMENTS

Figure 1:
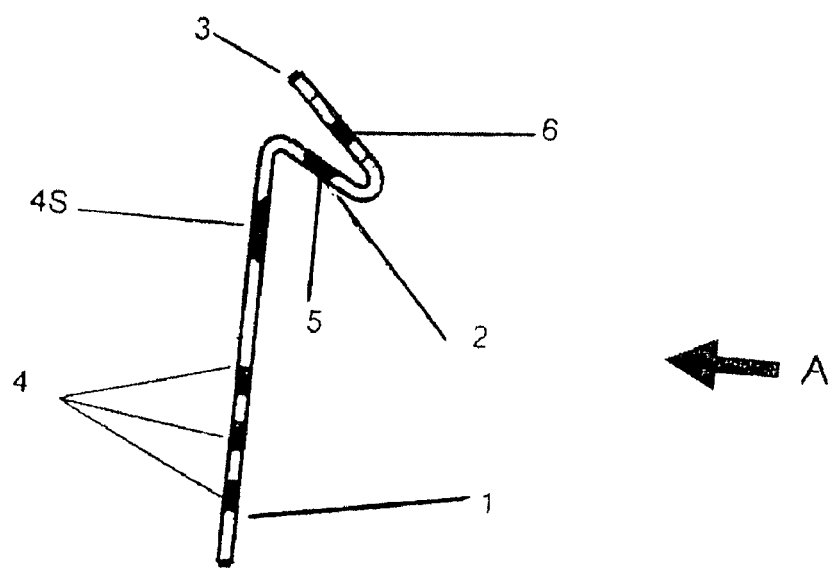
FIG. 1—is a side view of plate A.
Figure 2:
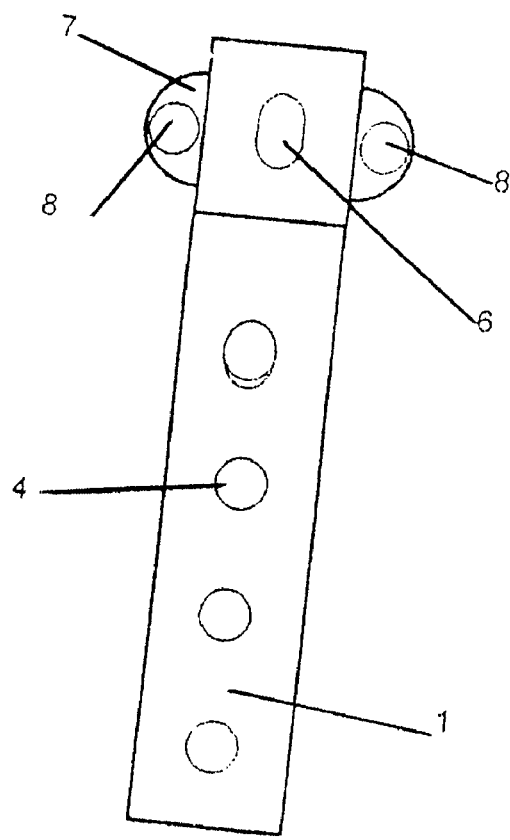
FIG. 2—is a front and top view of plate A, with two accessory side holes 8 in the upper blade 3.
Figure 3:
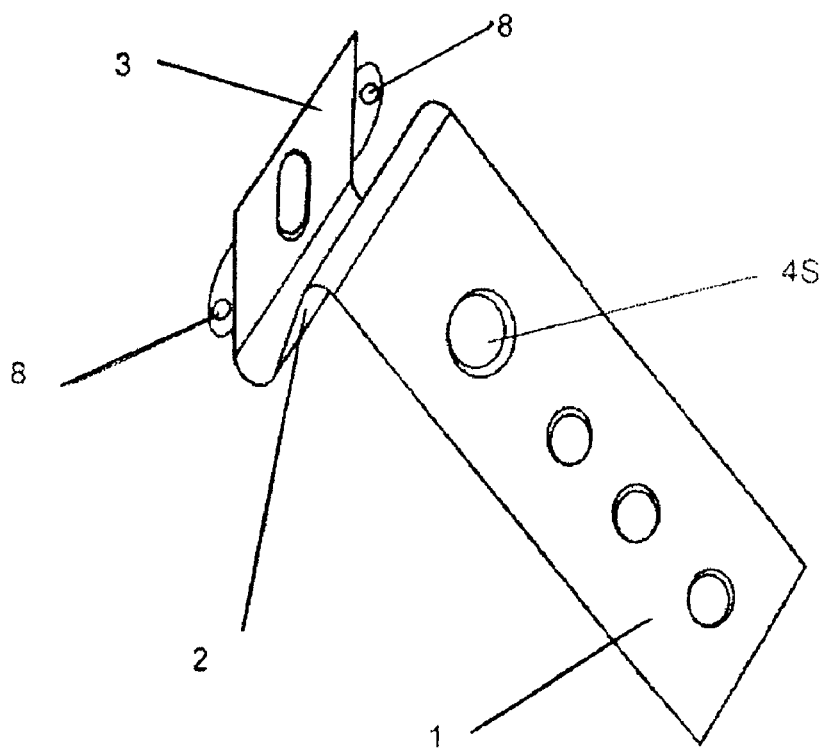
FIG. 3—is a top and oblique view of plate A, with two accessory side holes 8 in the upper blade 3.
Figure 4:
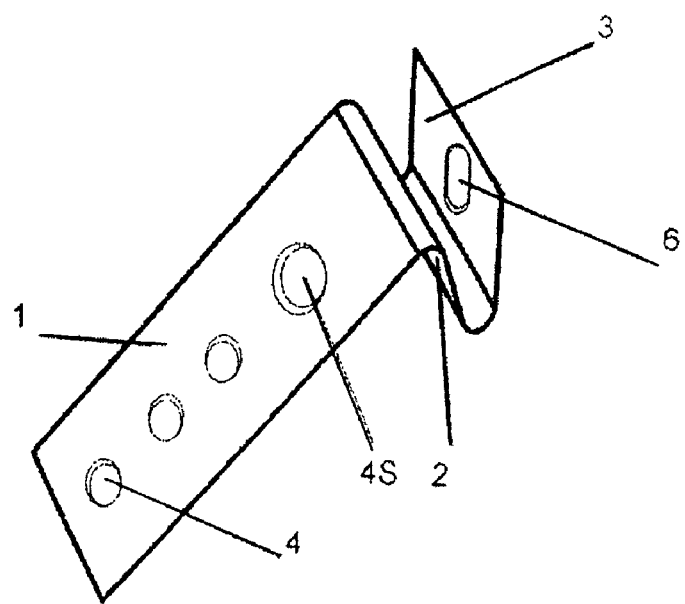
FIG. 4—is an oblique view of plate A.
Figure 5:
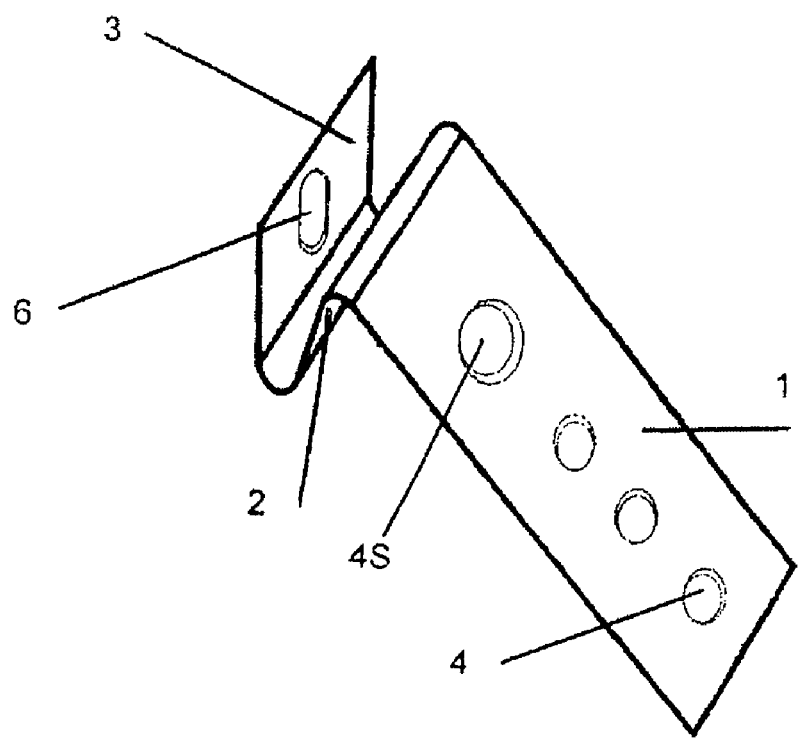
FIG. 5—is another oblique view of plate A.
Figure 6:
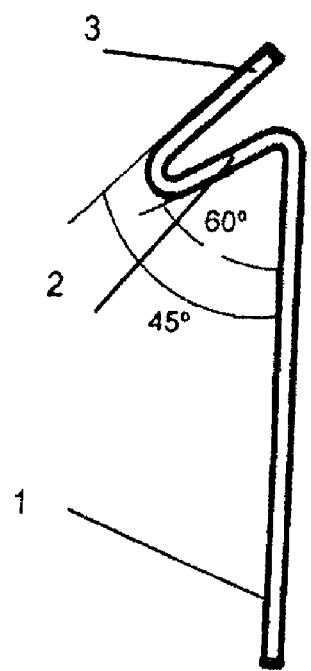
FIG. 6—is a side view of plate A with the angles of upper blade 3 and intermediate blade 2 in relation to blade 1 (longer and straighter segment).

The present invention is comprised of a set of plate and screws, whose shape allow the fastening and keeping of fractured fragments in an adequate position, preferably at the proximal end of the humerus bone (in the shoulder).

The present invention is comprised of a set of plate A and "interference" screw B, said screw B (not shown) being fixed to plate A.

Plate A is comprised of a blade 1, followed by an angled blade 2 and a third blade also angled 3, blades 2 and 3 forming a V-shaped segment. The angles between blades 1, 2 and 3 will vary depending on the kind of fracture and application of the plate. The angle formed between blade 1 and blade 2 is of 60° and between blade 1 and blade 3 of 45°.

Blade 1 has at least one hole, but preferably two or more holes 4, one of them being the oblong 4S. At least two holes 4 are for direct fastening to the fractured fragment. Hole 4S of blade 1 is oblong and allows screw B to penetrate this hole toward hole 5 of blade 2 and also toward hole 6 of blade 3. Screw B is fixed in the oblong hole 4S of blade 1. Depending on the desired fixation of the fractured bone fragments, the oblong hole 4S of blade 1, hole 5 of blade 2 and hole 6 of blade 3 may be present or not. The number of holes 4 is variable depending on the extension of the fracture and, therefore, of the needed fastening.

Blade 2 has hole 5 that works together with hole 6 of blade 3. In addition, blade 3 may have brims 7 provided with holes 8 for additional fastening to the fragments.

The length of blades 2 and 3 may vary depending on the extension of the fracture and, therefore, of the needed fastening, as well as the angulation.

The method of fastening the plate to the indicated location is simple, and is comprised of the preparation of the upper portion of the bone to be corrected through an opening, which may already exist because of the bone fracture, for the fitting of blades 2 and 3 of plate A and, in the longer fragment, or in the lower portion of the fractured segments, blade 1 is supported. Subsequently, holes are made for the fastening of conventional screws that pass through holes 4 and 8 of plate A. An inclined hole that allows the passage of screw B through hole 4S of blade 1, and then through hole 5 of blade 2 and through hole 6 of blade 3, is also made. Screw B will be screwed to the bone in one of its ends (distal) and in plate A through a thread in the blade where the screw head is fixed. The screws may be fixed to the plate or to the bone depending on the fixation needed or the kind of fracture.

Plate (A) and screw (B) are made preferably of metal, such as surgical steel, titanium, metal alloys, or bio-absorbable, or any other biocompatible material that promotes fastening and stabilization of the fracture.

The advantage of this invention in relation to the existing plate-blades is that the fractured fragments may be kept in position and in the angle desired and defined by the plate, for healing of the fracture.

The invention claimed is:

1. A bone fastening plate comprising a first blade and a second blade that form an angle between each other, and a third blade that forms an angle in relation to the first blade, the first, second and third blades curvedly arranged in the shape of an S, said first blade having at least one hole, said second blade having at least one hole and said third blade having at least one hole, said holes of the second and third blades being aligned for the passing of a fastening screw, wherein the first and second blades form an angle of about 60 degrees between each other; and the first and third blades form an angle of about 45 degrees between each other.

2. A bone fastening plate comprising a first blade and a second blade that form between each other an angle, and a third blade that forms an angle in relation to the first blade, the first, second and third blades curvedly arranged in the shape of an S, said first blade having at least one hole, said second blade having a hole and said third blade being provided with an oblong hole, said holes of the second and third blades being aligned for the passing of a fastening screw, the second blade extending from the first blade, which is fastenable to an outer portion of a bone, the second and third blades are insertable into a head portion of a bone and are arranged such that a space is defined between the second and third blades, wherein the first and second blades form an angle of about 60 degrees between each other; and the first and third blades form an angle of about 45 degrees between each other.

3. The plate, according to claim 2, wherein the plate and screw are made of a metal, surgical steel, titanium, metal alloys, a bio-absorbable, or any other biocompatible material that promotes fastening and stabilization of the fracture.

4. A bone fastening plate consisting of a first blade and a second blade that form an angle between each other, and a third blade that forms an angle in relation to the first blade, the first, second and third blades curvedly arranged in the shape of an S, said first blade having at least one hole, one of said at least one holes having an oblong shape, said second blade having a hole and said third blade being provided with a hole, said holes of the second and third blades and the hole having an oblong shape being aligned for the passing of a fastening screw, wherein the first and second blades form an angle of about 60 degrees between each other; and the first and third blades form an angle of about 45 degrees between each other.

5. The plate according to claim 4, wherein the plate and screw are made of a metal, surgical steel, titanium, metal alloys, a bio-absorbable, or any other biocompatible material that promotes fastening and stabilization of the fracture.

* * * * *